(12) United States Patent
Liu et al.

(10) Patent No.: US 11,379,742 B2
(45) Date of Patent: Jul. 5, 2022

(54) METHOD FOR PREDICTIVE SOIL MAPPING BASED ON SOLAR RADIATION IN LARGE FLAT AREA

(71) Applicants: INSTITUTE OF SOIL SCIENCE, CHINESE ACADEMY OF SCIENCES, Nanjing (CN); INSTITUTE OF FORENSIC SCIENCE OF CHINA, Beijing (CN)

(72) Inventors: Feng Liu, Nanjing (CN); Ganlin Zhang, Nanjing (CN); Zhenwen Sun, Nanjing (CN); Junya Wang, Nanjing (CN); Huayong Wu, Nanjing (CN); Zhao Zhao, Nanjing (CN); Xiaodong Song, Nanjing (CN)

(73) Assignees: INSTITUTE OF SOIL SCIENCE, CHINESE ACADEMY OF SCIENCES, Nanjing (CN); INSTITUTE OF FORENSIC SCIENCE OF CHINA, Beijing (CN)

(*) Notice: Subject to any disclaimer, the term of this patent is extended or adjusted under 35 U.S.C. 154(b) by 0 days.

(21) Appl. No.: 17/405,426

(22) Filed: Aug. 18, 2021

(65) Prior Publication Data
US 2022/0067553 A1   Mar. 3, 2022

(30) Foreign Application Priority Data
Aug. 25, 2020 (CN) .......................... 202010862190.3

(51) Int. Cl.
*G06N 5/04* (2006.01)
*G06F 17/18* (2006.01)
(Continued)

(52) U.S. Cl.
CPC ............... *G06N 5/04* (2013.01); *G01N 21/31* (2013.01); *G01N 33/24* (2013.01); *G06F 17/18* (2013.01); *G06N 20/20* (2019.01)

(58) Field of Classification Search
CPC .......... G06N 5/04; G06N 20/20; G01N 21/31; G01N 33/24; G01N 25/00; G01N 21/25; G06F 17/18; G06F 30/27; G06F 2119/08
See application file for complete search history.

(56) References Cited

PUBLICATIONS

Fathololoumi et al., Improved Digital Soil Mapping with Multitemporal Remotely Sensed Satellite Data Fusion: A Case Study in Iran, online Mar. 7, 2020, Science of the Total Environment 721, 14 pp. (Year: 2020).*

* cited by examiner

*Primary Examiner* — Toan M Le
(74) *Attorney, Agent, or Firm* — Dorsey & Whitney LLP

(57) ABSTRACT

The disclosure provides a method for predictive soil mapping based on solar radiation in large flat area, comprising: Step 1, capturing the response process of the earth's surface heat: after an observation day or an observation period is selected, a curve graph depicting a dynamic response of the surface heat to solar radiation captured by using a remote sensor of a moderate-resolution imaging spectrometer; Step 2, constructing environmental covariates: quantitative analysis is performed for the dynamic response curve graph obtained in Step 1 by a mathematical method, and characteristic parameters are extracted and taken as environmental covariates; and Step 3: a machine learning model is established for the predictive soil attribute mapping. This method solves the challenge of effective soil mapping in flat areas, significantly improves the accuracy and efficiency of predictive soil mapping in flat areas, reduces the cost in time and economy of soil survey mapping.

2 Claims, 2 Drawing Sheets

(51) Int. Cl.
*G06N 20/20* (2019.01)
*G01N 21/31* (2006.01)
*G01N 33/24* (2006.01)

METHOD FOR PREDICTIVE SOIL MAPPING BASED ON SOLAR RADIATION IN LARGE FLAT AREA

CROSS REFERENCE TO RELATED APPLICATION

This patent application claims the benefit and priority of Chinese Patent Application No. 202010862190.3, filed on Aug. 25, 2020, the disclosure of which is incorporated by reference herein, in its entirety, by this reference.

TECHNICAL FIELD

The present disclosure relates to a method for predictive soil mapping based on solar radiation in large flat area, and belongs to the field of predictive digital soil mapping.

BACKGROUND

Conventional soil mapping depends on individual skills and empirical knowledge obtained by soil survey experts through a large amount of field investigations. It takes polygons as basic cartographic expression and manually delineates different soil types or their combinations in certain spatial extent based on base maps such as topographic maps or aerial photographs. This method is low in mapping accuracy and efficiency but high in cost. The resulting polygon-based soil map does not match with other geographical element data (e.g., terrain, vegetation or remote sensing images) which are mainly represented by grid in the prior art. Moreover, it is difficult to update.

With the development of geographic information technologies such as digital terrain analysis, the predictive (digital) soil mapping has been gradually developed. It uses soil attributes and soil-forming factor data in digital format, adopts a quantitative soil-landscape model, takes grid as expression way, and generates digital soil maps by virtue of the computer. Grid representation allows the generated soil map to illustrate soil spatial variation in more detail, and the computer-assisted cartography with quantitative model enables more accurate soil mapping. At present, the predictive soil mapping technology is still in the research and development stage, and the structure of its models have developed from simple to complex, from classical statistics (multiple regression and discriminant analysis, etc.) to spatial statistical methods (ordinary Kriging, co-Kriging, regression Kriging, geographically weighted regression, etc.), and then to machine learning methods (cluster analysis, classification regression tree, support vector machine, artificial neural network, random forest, etc.) and the expert knowledge reasoning system. However, most of these methods are applied to mountainous and hilly areas with large topographic gradient, and no soil mapping method could be found for flat areas.

For flat areas, the simplest method is to obtain a large amount of soil samples and use ordinary Kriging and other spatial interpolation methods to generate spatially continuous soil map. But, the large amount of field survey samples cost too much, and it is unrealistic for regions with large areas or poor field accessibility.

The second method is the remote-sensing interpretation and classification technology. One way is to visually interpret a pseudo color synthesized images of Landsat™ and other remote-sensing multi-band images, and manually delineate polygons of different soil types to generate a soil distribution map. Another way is to automatically classify multi-band remote-sensing images in a computer by classification algorithms such as the maximum likelihood so as to generate a soil distribution map. However, it is often found that, by this method, the image separability of different cartographic units in flat areas is low, and the mapping accuracy is far lower than that in mountainous and hilly areas with larger topographic gradients. It is because that the correlation between observed vegetation conditions and soils is weak, and remote-sensing images cannot effectively capture dominant factor information of soil spatial variation in this area.

The third method is the soil spectral inversion technology, which establishes statistical models such as a multiple linear regression model between airborne or spaceborne visible-infrared spectral remote-sensing spectrum and a soil attribute based on soil sample points, so as to estimates the spatial distribution of soil attributes. However, multi-spectral remote sensing of this method is usually difficult to eliminate the composite influence due to vegetation. Its application is limited to bare soil areas, and it can only detect information of 3-5 mm of the soil surface.

To sum up, at present, the accuracy of predictive soil mapping in flat areas is usually low and cannot meet the application requirements of related industries for soil spatial information. No effective method has been proposed for the soil mapping of flat areas, which remains a challenge in the field of digital soil mapping.

SUMMARY

To solve the defects and shortcomings mentioned above in the prior art, the present disclosure provides a method for predictive soil mapping based on solar radiation in large flat area.

To solve the technical problem described above, the present disclosure provides a method for Predictive soil mapping based on solar radiation in large flat area, including:

Step 1, capturing the response process of the earth's surface heat: after an observation day or an observation period is selected, a curve graph depicting a dynamic response of the surface heat to solar radiation captured by using a remote sensor of a moderate-resolution imaging spectrometer;

Step 2, constructing environmental covariates: quantitative analysis is performed for the dynamic response curve graph obtained in Step 1 by a mathematical method, and characteristic parameters are extracted and taken as environmental covariates;

Step 3, a machine learning model is established for the predictive soil attribute mapping.

Among the above steps, the earth's surface temperature is used to characterize the surface heat state. The specific process of Step 1 is as follows:

1.1 Sunny days in spring, summer or autumn are chosen as observation days or periods, and the surface temperatures at five time points within 24 hours, namely 1:30, 10:30, 13:30, 22:30 on one day and 1:30 the next day, are recorded;

1.2 An earth's surface temperature changing curve graph is drawn by taking the time series as an independent variable and the surface temperature as a variable, which is the curve graph depicting the dynamic response of the earth's surface to the solar radiation.

The specific process of Step 2 is as follows:

2.1 The dynamic response curve graph of the surface to solar radiation is parameterized in two aspects of magnitude and shape;

2.11 In the aspect of magnitude, it is represented by the lowest surface temperature "bottom" and the highest surface temperature "plateau", the value of the lowest surface temperature "bottom" is the average value of the surface temperatures at 1:30 am on one day and 1:30 am the next day; the maximum surface temperature "plateau" is the average value of surface temperatures at 10:30 am and 13:30 pm.

2.12 In the aspect of morphology, it is represented by the gradient angle index "angleslp", and the gradient angle indexes at five time points of 1:30, 10:30, 13:30, 22:30 on one day and 1:30 the next day are calculated respectively. Taking 10:30 as an example, the gradient angle index angleslp$_{10:30}$ at the time point of 10:30 is calculated as follows:

$$\beta_{10:30} = \cos^{-1}\left[\frac{a^2 + b^2 - c^2}{2ab}\right]$$

$$angleslp_{10:30} = \beta_{10:30} * \text{slope}$$

In the formula, a, b and c are Euclidean distances between two adjacent time points of three time points of 1:30, 10:30 and 13:30 on one day in the surface temperature changing curve graph, $\beta_{10:30}$ is the radian angle at 10:30, "slope" is the slope of line segment c, and the time distance between two adjacent time points is 1;

By the same calculation method, the gradient angle indexes angleslp$_{13:30}$ and angleslp$_{22:30}$ at 13:30 and 22:30 are calculated respectively;

2.2 Statistics is performed on the five environmental covariates calculated in Step 2.1: the lowest surface temperature "bottom", the highest surface temperature "plateau", the gradient angle index angleslp$_{10:30}$ at 10:30, the gradient angle index angleslp$_{13:30}$ at 13:30, and the gradient angle index angleslp$_{22:30}$ at 22:30.

The specific process of Step 3 is as follows:

3.1 A relationship model between soil attributes and environmental covariates is established by using the random forest algorithm;

3.2 Applying the relationship model established in Step 3.1 to all mapping areas: the environmental covariate value at a certain geographical location in the mapping area is substituted into the relationship model established in Step 3.1, so as to obtain a predicted value of soil attributes at this geographical location;

3.3 After traversing all locations, the spatial distribution map of soil attributes across all mapping areas can be obtained.

The present disclosure achieves the following beneficial effects: the present disclosure provides a method for predictive soil mapping in a flat area. This method solves the challenge of effective soil mapping in flat areas, significantly improves the accuracy and efficiency of predictive soil mapping in flat areas, reduces the cost in time and economy of soil survey mapping, and thus can meet the application requirements of soil related industries for accurate soil spatial information.

DETAILED DESCRIPTION OF THE EMBODIMENTS

The present disclosure will be further described with reference to specific embodiments below. The following embodiments are only for the purpose of illustrating technical schemes of the present disclosure more clearly, but cannot limit the protection scope of the present disclosure.

The present disclosure will be further described with reference to figures and embodiments below.

The present disclosure provides a method for Predictive soil mapping based on solar radiation in large flat area, including:

Step 1, capturing the response process of the earth's surface heat: after an observation day or an observation period is selected, a curve graph depicting a dynamic response of the surface heat to solar radiation captured by using a remote sensor of a moderate-resolution imaging spectrometer;

In namely spring, summer or autumn, solar radiation in sunny days of these three seasons has relatively high magnitudes, which allows the earth surface to produce obvious response, namely clear surface heat response. The MODIS (Moderate Resolution Imaging Spectrometer) remote sensor of Terra and Aqua satellites in the United States with a high temporal resolution is used to observe and capture the dynamic response of the surface to solar radiation within one day, which is embodied by the change of surface heat state in time series. That is, the surface temperature is used to characterize the surface heat state: the MODIS sensor, MOD11A1, carried by the Terra satellite obtains daily surface temperature data with 1 km resolution, including image data at two time points of 10:30 am and 22:30 μm. The MODIS sensor MYD11A1 carried by the Aqua satellite acquired daily surface temperature data with 1 km resolution, including the image data at two time points of 13:30 pm and 01:30 am the next day, thus obtaining the changing rule of surface temperature within 24 hours.

Figure 1:
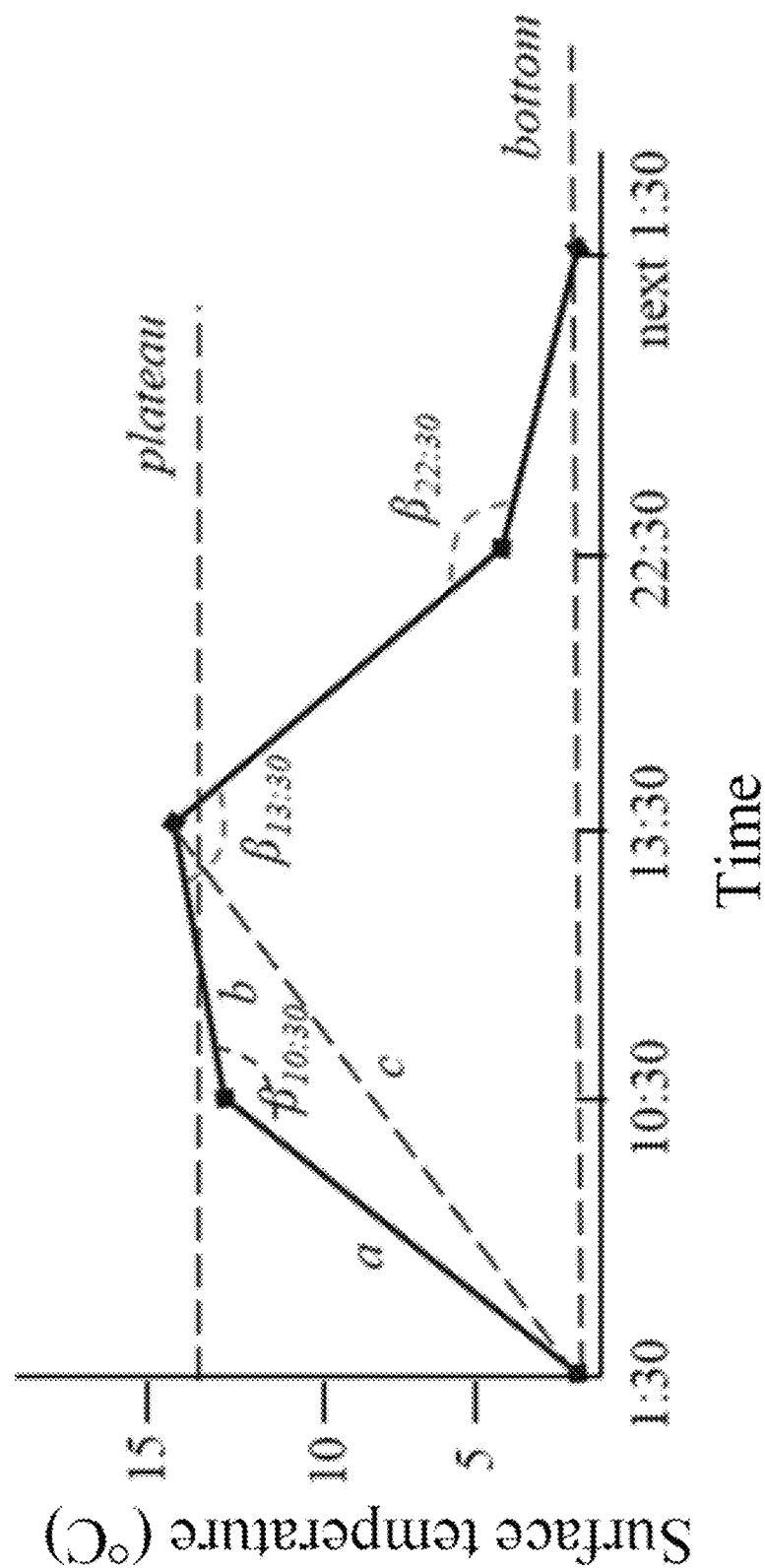
FIG. 1 is a curve graph of surface temperature changing according to the present disclosure.

The specific process is as follows:

1.1 According to factors such as temperature and precipitation displayed by daily meteorological data sunny days in spring, summer or autumn are chosen as observation days or periods, and the surface temperatures at five time points within 24 hours, namely 1:30, 10:30, 13:30, 22:30 on one day and 1:30 the next day, are recorded;

1.2 An earth's surface temperature changing curve graph is drawn by taking the time series as an independent variable and the surface temperature as a variable, which is the curve graph depicting the dynamic response of the earth's surface to the solar radiation, as shown in FIG. 1.

Step 2, constructing environmental covariates: quantitative analysis is performed for the dynamic response curve graph obtained in Step 1 by a mathematical method, and characteristic parameters are extracted and taken as environmental covariates. The specific process of Step 2 is as follows:

2.1 The dynamic response curve graph of the surface to solar radiation is parameterized in two aspects of magnitude and shape;

2.11 in the aspect of magnitude, it is represented by the lowest surface temperature "bottom" and the highest surface temperature "plateau", the value of the lowest surface temperature "bottom" is the average value of the surface temperatures at 1:30 am on one day and 1:30 am the next day;

the maximum surface temperature "plateau" is the average value of surface temperatures at 10:30 am and 13:30 pm.

2.12 In the aspect of morphology, it is represented by the gradient angle index "angleslp", and the gradient angle indexes at five time points of 1:30, 10:30, 13:30, 22:30 on one day and 1:30 the next day are calculated respectively. Taking 10:30 as an example, the gradient angle index $angleslp_{10:30}$ at the time point of 10:30 is calculated as follows:

$$\beta_{10:30} = \cos^{-1}\left[\frac{a^2 + b^2 - c^2}{2ab}\right]$$

$$angleslp_{10:30} = \beta_{10:30} * slope$$

In the formula, as shown in FIG. 1, a, b and c are Euclidean distances between two adjacent time points of three time points of 1:30, 10:30 and 13:30 on one day in the surface temperature changing curve graph, $\beta_{10:30}$ is the radian angle at 10:30, "slope" is the slope of line segment c, and the time distance between two adjacent time points is 1. If the surface temperature rises slowly in the morning (before 10:30), the gradient angle will approach π; if the temperature rises rapidly during this period, the surface temperature at 10:30 is already close to the highest surface temperature of the day, and this angle will be close to π/2. A high gradient angle index value represents a large and rapid increase in overall surface temperature.

By the same calculation method, the gradient angle indexes $angleslp_{13:30}$ and $angleslp_{22:30}$ at 13:30 and 22:30 are calculated respectively. The gradient angle index $angleslp_{10:30}$ reflects the characteristics of the surface temperature rising under solar radiation, $angleslp_{01:30}$ reflects the characteristics of the surface temperature rising first and then falling, and $angleslp_{22:30}$ reflects the characteristics of the surface temperature falling.

2.2 Statistics is performed on the five environmental covariates calculated in Step 2.1: the lowest surface temperature "bottom", the highest surface temperature "plateau", the gradient angle index $angleslp_{10:30}$ at 10:30, the gradient angle index $angleslp_{13:30}$ at 13:30, and the gradient angle index $angleslp_{22:30}$ at 22:30.

Step 3: a machine learning model is established for the predictive soil attribute mapping. The specific process of Step 3 is as follows:

3.1 A relationship model between soil attributes and environmental covariates is established by using the random forest algorithm. By collecting soil survey samples, a relationship model with environmental covariates (bottom, plateau, $angleslp_{10:30}$, $angleslp_{13:30}$, $angleslp_{22:30}$) is established. The random forest algorithm is adopted, which is a collective machine learning algorithm composed of multiple regression or classification tree models, it can deal with complex soil environment relations, and it functions more accurately and stably when samples are limited. Among the algorithm parameters, the number of variables "mtry" of a binary tree with single tree nodes is set to 3, the number "ntree" of single trees is set to 500, and the minimum value "minnode" of single tree endpoints is set to 5. Calling random forest package to build a model in R software environment 3.2 Applying the relationship model established in Step 3.1 to all mapping areas: the environmental covariate value at a certain geographical location in the mapping area is substituted into the relationship model established in Step 3.1, so as to obtain a predicted value of soil attributes at this geographical location;

3.3 After traversing all locations, the spatial distribution map of soil attributes across all mapping areas can be obtained.

According to the present disclosure, solar radiation is used as an input to the earth surface, and the earth surface will generate a dynamic response to the solar radiation. As for flat areas, the solar radiation can be regarded to be uniform in a larger space range; while under the same terrain and vegetation condition, the response will mainly depend on soil attributes. Therefore, the surface dynamic response based on solar radiation can reflect the difference of soil spatial environment covariates, and accurately map the soil attributes in large flat areas. This method solves the challenge of effective soil mapping in flat areas, significantly improves the accuracy and efficiency of predictive soil mapping in flat areas, reduces the cost in time and economy of soil survey mapping, and thus can meet the application requirements of soil related industries for accurate soil spatial information.

EMBODIMENTS

Figure 2B:
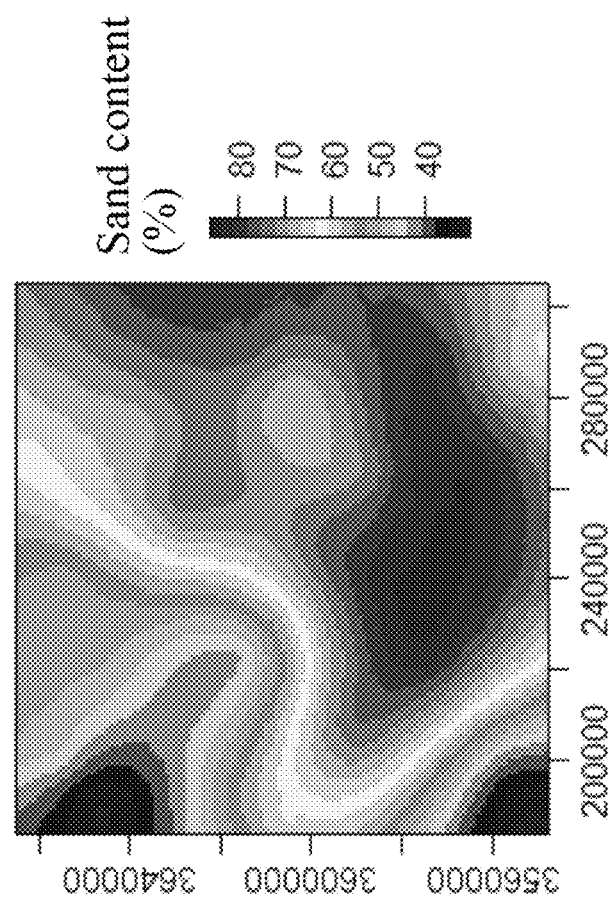
FIG. 2 is a comparison between the soil spatial distribution maps prepared by the method of the present disclosure (FIG. 2a) and by the ordinary Kriging spatial interpolation method (FIG. 2b) in the specific embodiment.
Figure 2A:
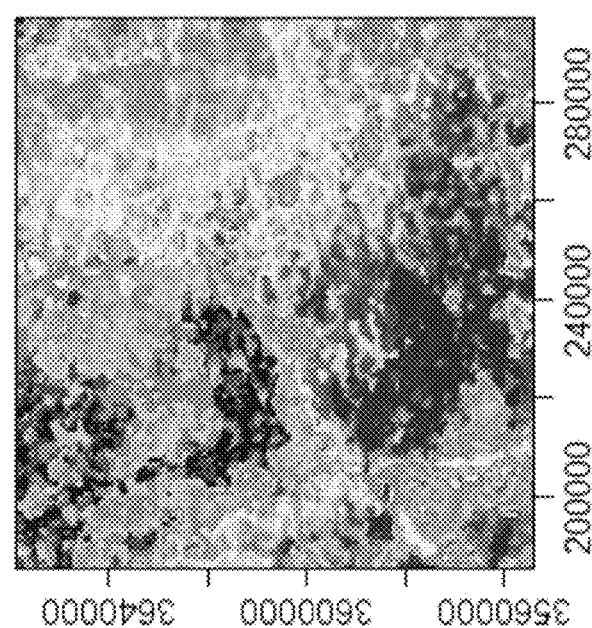

In order to illustrate the technical effect of the present disclosure, a plain area in the middle of Jiangsu Province is taken as an example of mapping area for illustration, and the specific steps are as follows:

Referring to the daily meteorological data, Nov. 28, 2014 is selected as the observation period;

Remote-sensing data MOD11A1 and MYD11A1 of surface temperature by MODIS (moderate Resolution Imaging Spectrometer) during the observation period is acquired, and the curve graph of surface temperature changing within 24 hours is obtained;

Parameterized calculation is carried out on the surface temperature changing curve graph of each pixel location in the area to be researched, so as to obtain five parameter values: bottom, plateau, $angleslp_{10:30}$, $angleslp_{13:30}$ and $angleslp_{22:30}$. After traversing all locations, a group of environmental covariates of the whole research area are generated accordingly. Data analysis shows that the correlation coefficients between the constructed environmental variables and the surface soil texture, organic matter content, and soil pH are all above 0.6;

Based on 144 grid survey soil sample points, the environmental covariate values of these sample points are extracted. In the R software environment, a random Forest function package is called to establish a random forest model between the sand content in surface soil and the environmental variables;

Map layer data files of the constructed environmental covariates (bottom, plateau, $angleslp_{10:30}$, $angleslp_{13:30}$ and $angleslp_{22:30}$) are read and input as a model which is then executed at each location in the mapping area, so as to obtain soil attribute prediction results of all locations and generate a sand content distribution map of surface soil in the mapping area. The results are as shown in the left figure of FIG. 2 (FIG. 2a and FIG. 2b).

The accuracy of cartographic results is evaluated by the method of leaving one cross-validation (LOOCV), wherein one sample point is left as a test point at a time, and all other sample points are used for modeling, and the soil attributes of the test points are predicted, so as to obtain the predicted values of all sample points and compare them with the observed values, thus calculating the cartographic accuracy index $R^2$ and RMSE, etc. The results show high cartographic accuracy, wherein the soil texture cartographic accuracy $R^2$ reaches 0.71 and RMSE reaches 7.5%.

In conclusion, the results indicate that:

Firstly, the correlation coefficients between the constructed environmental covariates and the surface soil texture, the organic matter content and the soil pH are all above 0.6, which indicates that the constructed environmental covariates are quite able to indicate the spatial differences of soil attributes;

Secondly, in a 12000 km² plain area, in the case of only 144 grid survey sample points, the determination coefficient $R^2$ of soil texture cartographic accuracy obtained by the random forest algorithm reaches 0.71, the RMSE reaches 7.5%; and in the case of only 11 representative survey sample points, the cartographic accuracy of soil texture obtained by the CBR algorithm also reaches the same level. This indicates that the present disclosure can achieve a better mapping accuracy and higher efficiency simply by collecting a small amount of limited soil samples, which significantly reduces the workload of soil investigation and saves time and economic expenses. Compared with conventional soil investigation and cartographic technologies, the accuracy is improved by 20%, the speed is increased by at least 10 times, and the cost is reduced by about ⅔.

Thirdly, the spatial fineness of the mapping results is significantly higher than that obtained by the ordinary Kriging spatial interpolation method. As shown in FIG. 2 (FIG. 2a and FIG. 2b), in the case of using the same 144 soil samples, the mapping results of the present disclosure are rich in spatial details, while results obtained by ordinary Kriging interpolation only have a rough spatial distribution trend, indicating that the cartographic effect of the present disclosure is better than that of the conventional methods.

The present disclosure has been disclosed with the preferred embodiments above without limiting the present disclosure. All technical solutions obtained by adopting equivalent alterations or equivalent variant schemes fall within the protection scope of the present disclosure.

What is claimed is:

1. A method for predictive soil mapping based on solar radiation in large flat area, the method comprising:
    capturing a response process of earth's surface heat: after an observation day or period is selected, a curve graph depicting a dynamic response of the surface heat to solar radiation captured by using a remote sensor of a moderate-resolution imaging spectrometer;
    constructing environmental covariates: quantitative analysis is performed for the dynamic response curve graph obtained in the capturing step by a mathematical method, and characteristic parameters are extracted and taken as environmental covariates; and
    establishing a machine learning model for predictive soil attribute mapping,
    wherein constructing the environmental covariates comprises:
        parameterizing the dynamic response curve graph of the surface to solar radiation in two aspects of magnitude and shape;
        wherein in the aspect of magnitude, it is represented by a lowest surface temperature "bottom" and a highest surface temperature "plateau", a value of the lowest surface temperature "bottom" is an average value of surface temperatures at 1:30 am on one day and 1:30 am on next day; a maximum surface temperature "plateau" is an average value of surface temperatures at 10:30 am and 13:30 pm on the one day,
        wherein in the aspect of morphology, it is represented by a gradient angle index "angleslp", and the gradient angle indexes at five time points of 1:30, 10:30, 13:30, 22:30 on the one day and 1:30 on the next day are calculated respectively, wherein the gradient angle index $angleslp_{10:30}$ at 10:30 is calculated as follows:

$$\beta_{10:30} = \cos^{-1}\left[\frac{a^2 + b^2 - c^2}{2ab}\right]$$

$$angleslp_{10:30} = \beta_{10:30} * slope$$

in the formula, a, b and c are Euclidean distances between two adjacent time points of three time points of 1:30, 10:30 and 13:30 on the one day in the surface temperature changing curve graph, $\beta_{10:30}$ is a radian angle at 10:30, "slope" is a slope of a line segment c, and a time distance between the two adjacent time points is 1;

by the same calculation method, the gradient angle indexes, $angleslp_{13:30}$ and $angleslp_{22:30}$, at 13:30 and 22:30 are calculated respectively;

performing statistics on the five environmental covariates calculated in the parameterizing step: the lowest surface temperature "bottom", the highest surface temperature "plateau", the gradient angle index $angleslp_{10:30}$ at 10:30, the gradient angle index $angleslp_{13:30}$ at 13:30, and the gradient angle index $angleslp_{22:30}$ at 22:30; and wherein, establishing the machine learning model for the predictive soil attribute mapping comprises:
    establishing a relationship model between soil attributes and the environmental covariates by using a random forest algorithm;
    applying the established relationship model to all mapping areas: an environmental covariate value at each geographical location in the mapping areas is substituted into the established relationship model, to obtain a predicted value of the soil attributes at the geographical location; and
    obtaining a spatial distribution map of the soil attributes across all mapping areas after traversing all locations.

2. The method according to claim 1, wherein the earth's surface temperature is used to characterize a surface heat state, and the capturing step includes:
    choosing a sunny day in spring, summer or autumn as the observation day or period, and recording the surface temperatures at five time points within 24 hours including 1:30, 10:30, 13:30, 22:30 on one day and 1:30 on the next day; and
    drawing an earth's surface temperature changing curve graph by taking the time series as an independent variable and the surface temperature as a variable, which is the curve graph depicting the dynamic response of the earth's surface to the solar radiation.

* * * * *